United States Patent [19]

Black et al.

[11] Patent Number: 4,863,966
[45] Date of Patent: Sep. 5, 1989

[54] PESTICIDAL AMINES

[75] Inventors: Malcolm H. Black, Tring; Alexander D. Frenkel, Aston Clinton; Peter T. Roberts, Berkhamsted, all of England

[73] Assignee: Burroughs Wellcome Co., Research Triangle Park, N.C.

[21] Appl. No.: 234,908

[22] Filed: Feb. 17, 1981

[30] Foreign Application Priority Data

Feb. 21, 1980 [GB] United Kingdom ............... 8005887

[51] Int. Cl.⁴ ............... A01N 33/02; C07C 153/05; C07D 207/08; C07D 211/00
[52] U.S. Cl. ............... 514/599; 514/183; 514/212; 514/317; 514/428; 514/524; 514/519; 514/520; 514/331; 514/523; 564/74; 548/568; 548/300; 548/341; 548/352; 548/215; 548/239; 548/240; 546/184; 546/233; 546/230; 544/106; 544/160; 544/358; 544/400; 558/393; 558/418
[58] Field of Search ............... 514/183, 212, 317, 428, 514/524, 519, 520, 599, 331, 523; 260/239 BF; 564/74; 548/568, 300, 341, 352, 215, 239, 240, 146, 214; 546/184, 233; 544/106, 160, 358, 400; 424/256, 263, 267, 274, 320, 244

[56] References Cited

U.S. PATENT DOCUMENTS

| | | | |
|---|---|---|---|
| 2,579,478 | 12/1951 | Djerassi et al. | 544/53 |
| 3,647,413 | 3/1972 | Rumanowski | 71/98 |
| 3,725,452 | 4/1973 | Rumanowski | 260/453 R |
| 4,131,449 | 12/1978 | Entwistle | 71/98 |
| 4,226,876 | 10/1980 | Copp et al. | 424/273 R |
| 4,238,497 | 12/1980 | Black et al. | 424/273 R |

FOREIGN PATENT DOCUMENTS

| | | | |
|---|---|---|---|
| 862022 | 6/1978 | Belgium | 424/273 R |
| 19294 | 11/1980 | European Pat. Off. | 424/273 R |
| 2756638 | 6/1978 | Fed. Rep. of Germany | 424/273 R |
| 1374682 | 8/1964 | France | 424/273 R |
| 2023603 | 1/1980 | United Kingdom | 424/273 R |

Primary Examiner—Mary C. Lee
Assistant Examiner—Robert C. Whittenbaugh
Attorney, Agent, or Firm—Donald Brown

[57] ABSTRACT

Compounds of formula (I) are pesticides having activity against arthropods:

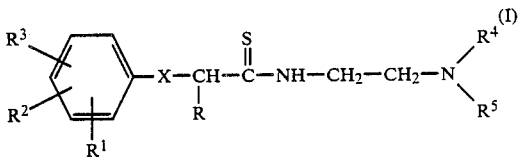

wherein
$R^1$, $R^2$ and $R^3$ are H, alkyl, alkoxy, halo, cyano or trifluoromethyl, or two of $R^1$, $R^2$ and $R^3$ are linked to form a 3 or 4 carbon atom group;
X is O or NA where A is H or alkyl;
R is H or alkyl; and
$R^4$ and $R^5$ are H, alkenyl or haloalkenyl or optionally substituted alkyl, aryl or aralkyl, or $NR^4R^5$ represents a heterocyclic ring; or an acid addition salt thereof.

The invention further provides methods for the preparation of the compounds, pesticidal formulations containing them, and their use in controlling arthropod pests.

54 Claims, No Drawings

PESTICIDAL AMINES

This invention relates to compounds having activity against arthropods, processes for their preparation, intermediates useful in these processes, pesticidal formulations containing the compounds, and the use of the compounds as pesticides.

We have discovered that the compounds of formula (I) below and their acid addition salts have activity against arthropods, particularly members of the Order Acarina.

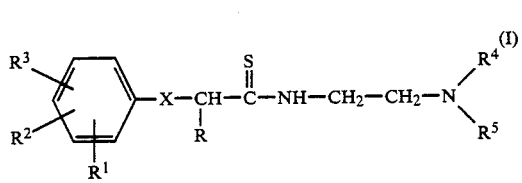

In formula (I), $R^1$, $R^2$ and $R^3$ are the same or different and are selected from hydrogen, alkyl, alkoxy, halo, cyano and trifluoromethyl, or two of $R^1$, $R^2$ and $R^3$ are linked to form a 3 or 4 carbon atom group;

X is O or NA where A is hydrogen or alkyl;

R is hydrogen or alkyl; and $R^4$ and $R^5$ are the same or different and are selected from hydrogen; alkyl; substituted alkyl wherein the substituent(s) are selected from halo, cyano, alkoxy, aryloxy, alkylthio, arylthio and substituted and unsubstituted amino; alkenyl; haloalkenyl; aryl; aralkyl or substituted aryl or aralkyl wherein the substituents are selected from halo, alkyl, alkoxy, cyano and trifluoromethyl; or $NR^4R^5$ represents a heterocyclic ring containing from 4 to 10 ring atoms.

When used herein, 'alkyl' and 'alkoxy' mean a straight or branched alkyl or alkoxy group, respectively, having from 1 to 20, such as 1 to 5 carbon atoms; 'halo' means fluoro, chloro, bromo or iodo; 'aryl' means a phenyl or naphthyl group; 'aralkyl' means an alkyl groups as defined above substituted by a phenyl or napththyl group; and 'alkenyl' is a $C_{3-20}$, such as $C_{3-5}$, alkenyl group saturated in the 1-position, such as prop-2-enyl.

Suitable heterocyclic groups $NR^4R^5$ include pyrrolidino, piperidino, morpholino, piperazino, 1-imidazoline, 3-oxazoline and 3-thiazoline.

Preferred compounds of the invention include those having one or more of the following features:

at least one of $R^1$, $R^2$ and $R^3$ is alkyl, such as methyl, or halo, such as chloro, particularly those compounds where $R^3$ is hydrogen and $R^1$ and $R^2$ are in the 2- and 3-positions;

X is O or NH;

$R^4$ is hydrogen or alkyl, such as methyl;

$R^5$ is alkyl, such as methyl; or $NR^4R^5$ represents a pyrrolidino or piperidino group.

The compounds of formula (I) may be prepared by conventional methods used for the preparation of compounds having analogous chemical structures.

These methods include:

(a) the reaction of a compound of formula (III):

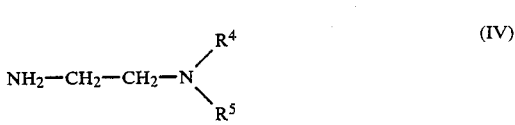

wherein $R^1$, $R^2$, $R^3$, X and R are as defined in formula (I) and Z is a leaving group such as alkoxy, alkylthio, aralkoxy, aralkylthio or mercapto with a compound of formula (IV):

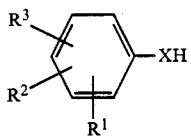

or a salt thereof wherein $R^4$ and $R^5$ are as defined in formula (I);

(b) the reaction of a phenol or aniline of formula (V):

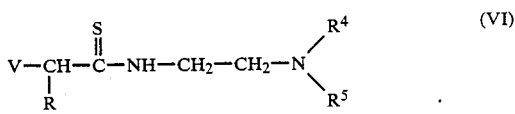

or an O- or N-metal derivative thereof (such as an alkali metal derivative) wherein X, $R^1$, $R^2$ and $R^3$ are as defined in formula (I) with a compound of formula (VI):

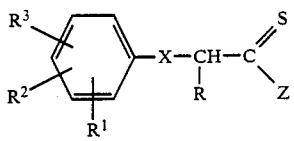

wherein R, $R^4$ and $R^5$ are as defined in formula (I) and V is a leaving group derived from a suitable organic or inorganic acid, such as halo (e.g. chloro, bromo or iodo), alkylsulphonyloxy or arylsulphonyloxy (e.g. p-toluenesulphonyloxy);

(c) the reaction of a compound of formula (VII):

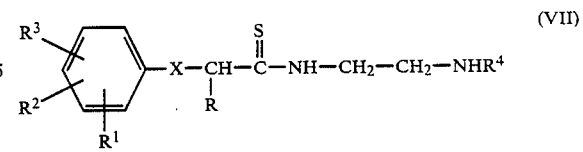

wherein $R^1$, $R^2$, $R^3$, X, R and $R^4$ are as defined in formula (I) with a compound of formula (VIII):

$$W-R^5 \qquad (VIII)$$

wherein $R^5$ is as defined in formula (I) and W is a leaving group such as halo:

(d) the reaction of a compound of formula (IX):

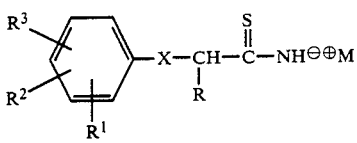

wherein $R^1$, $R^2$, $R^3$, X and R are as defined in formula (I) and $M^\oplus$ is one equivalent of a metal ion, such as $K^\oplus$ or $Na^\oplus$ with a compound of formula (X):

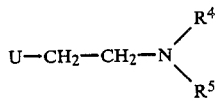

wherein $R^4$ and $R^5$ are as defined in formula (I) and U is a leaving group such as those defined above for the group V in formula (VI);

(e) the reaction of a compound of formula (XI):

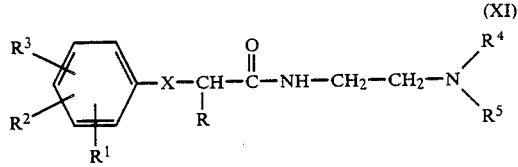

wherein $R^1$, $R^2$, $R^3$, X, R, $R^4$ and $R^5$ are as defined in formula (I) with $P_2S_5$ or other inorganic sulphide and (f) the reaction of a compound of formula (XII):

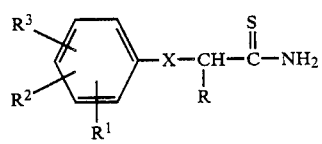

wherein $R^1$, $R^2$, $R^3$, X and R are as defined in formula (I) or a compound of formula (IX) as hereinbefore defined with a compound of formula (XIII):

wherein $R^4$ is as defined in formula (I), and thereafter, if desired, reacting the product with a compound of formula (VII) as hereinbefore defined.

The compounds of formula (I) may be isolated from the reaction mixture as the free base or in the form of an acid addition salt. The bases may be converted into acid addition salts thereof by known techniques with the aid of the appropriate acid, and salts of the compounds may also be converted into the free bases or into other acid addition salts. For use as a pesticide, the compounds of formula (I) may be represented in the form of their free bases, or as acid addition salts thereof. Suitable salts of formula (I) include hydrohalide, sulphate, nitrate, phosphate, thiocyanate, acetate, propionate, stearate, naphthenate, perchlorate, benzoate, methanesulphonate, ethanesulphonate, tosylate and benzenesulphonate acid addition salts thereof.

The compounds of formula (I) may be used to combat insects, ticks, mites and other arthropods including free living arthropods and those which are ectoparasites of plants, mammals and birds. They are especially useful for the control of acarine ectoparasites of animals, particularly those ticks of the genera Boophilus, Rhipicephalus, Amblyomma, Hyalomma, Ixodes, Haemaphysalis, Dermacentor, and Anocentor; mites of veterinary importance, such as Psoroptes spp., Psorergates spp., Sarcoptes spp., Chorioptes spp. and Demodex spp., e.g. the sheep scab mite *Psoroptes ovis;* and other ectoparasites of the sub-Orders Ixodoidea and Sarcoptiformes; and Tetranychus species on plants. Such ectoparasites infest stock and domestic animals and fowls, depending upon the location of the host and the particular ectoparasite. Common hosts are cattle, pigs, sheep, goats, horses, camels, chickens, dogs and cats.

The compounds of formula (I) may be used alone or in combination with an additive which may take the form of one or more of the carriers used in the formulation art, such as: wetting, diluting, stabilising, thickening, emulsifying, dispersing or surface active agents or other standard carrier ingredients.

A formulation may be an aqueous solution of an acid addition salt of a compound of formula (I), or a suspension of a compound of formula (I) in water, and may be used alone or in combination with suitable surface active agents. The formulation per se may be used alone or diluted in water for application to the pests or their immediate environment by way of spraying, dipping, or other known means of application.

A formulation may be in the form of a water miscible oil comprising a compound of formula (I) per se or, when X is NA, with an equimolar quantity of a suitable organic acid, such as oleic acid or naphthenic acid, to provide a salt soluble in organic solvents and emulsifiers, and is applied as an emulsion by way of spraying or dipping.

A formulation may be a non-aqueous solution or suspension of compound (I) in a suitable organic solvent for the direct application by the 'pour-on' method. A formulation may also take the form of a wettable powder for dilution with water and application by dipping or spraying. Other solid formulations may also be used for direct application without dilution such as dusts, powders and granules.

A further formulation may be a paste, grease or gel containing a compound of formula (I) and a suitable carrier, and may be applied by spreading the formulation over the infested area.

A compound of formula (I) is preferably present in a pesticidal formulation in an amount between 5 and 80%, particularly preferred formulations containing about 20%, calculated by weight of the compound (I) per se. The concentration of a compound of formula (I) applied to the pests or their immediate environment may be in the range of 0.001%–20%, calculated by weight of the compound (I) per se.

It will be appreciated from the foregoing that what we will claim may comprise any novel feature described herein, principally and not exclusively, for example:

(a) A compound of formula (I) or an acid addition salt thereof;

(b) A method of preparation of a compound of formula (I) or an acid addition salt thereof;

(c) A method of controlling arthropod pests, particularly members of the Order Acarina, by applying to the pest or the pest's environment a compound of formula (I) or an acid addition salt thereof;

(d) A pesticidal formulation comprising a compound of formula (I) or an acid addition salt thereof and a carrier therefor;

(e) A method of making a formulation comprising admixture of a carrier and a compound of formula (I) or an acid addition salt thereof;

(f) A compound of formula (I) or an acid addition salt thereof for use as a pesticide;

(g) Novel intermediates used in processes (a)-(f)

EXAMPLE 1

N-(2-Pyrrolidinoethyl)-(2,3-dimethylphenoxy)-thioacetamide (i) A stirred suspension of O-ethyl(2,3-dimethylphenoxy)-acetimidate hydrochloride (13 g) in dry ether (100 ml) was treated with dry triethylamine (5.39 g). The resultant mixture was treated with dry gaseous hydrogen sulphide for 2 hr at 0° C. and set aside at 0°-5° C. overnight. The resulting solids were removed by filtration and the filtrate evaporated to dryness to yield ethyl thiono-(2,3-dimethylphenoxy)-acetate as a colourless solid, mp 39°-40° C. (ii) A solution of 1-(2-aminoethyl)-pyrrolidine (2.04 g) in dry ether (10 ml) was added dropwise to a stirred solution of ethyl thiono-(2,3-dimethylphenoxy)acetate (4.41 g) in dry ether (40 ml) at ambient temperature. After 1-2 hours when tlc analysis indicated completion of reaction, the solvent was removed under reduced pressure and the resulting solid recrystallised from hexane to yield the title product, mp 62°-64° C.

EXAMPLE 2

N-[(2,3-dimethylphenoxy)thioacetyl]-ethane-1,2-diamine, perchlorate salt (i) Ethyl thiono-(2,3-dimethylphenoxy)acetate was prepared as in Example 1.

(ii) The ethylthiono(2,3-dimethylphenoxy)acetate (2.70 g 5% molar excess) was added dropwise in dry ethereal solution to a dry ethereal solution of 1,2-diaminoethane (0.66 g) at 0° C. After 1-2 hours tlc analysis indicated completion of reaction. A concentrated aqueous solution of perchloric acid was then added dropwise to this solution with stirring until the resulting mixture just became acidic (to universal indicator paper). The salt was isolated by filtration to give the title product, mp 183° C.

EXAMPLES 3 TO 17

By methods analogous to those described in Examples 1 or 2 above, the compounds of Examples 3 to 17 below were also prepared.

EXAMPLE 3: N-[(2,3-dimethylphenoxy)thioacetyl]-N'-methyl-ethane-1,2-diamine; mp 74°-75° C.

EXAMPLE 4: N-[(2,3-dimethylphenoxy)thioacetyl]-N',N'-dimethyl-ethane-1,2-diamine; mp 81° C.

EXAMPLE 5: N-(2-Piperazinoethyl)-(2,3-dimethylphenoxy)-thioacetamide; mp 119°-121° C.

EXAMPLE 6: N-(2-Piperidinoethyl)-(2,3-dimethylphenoxy)-thioacetamide; mp 89°-91° C.

EXAMPLE 7: N-(2-Morpholinoethyl)-(2,3-dimethylphenoxy)-thioacetamide; mp 105°-106° C.

EXAMPLE 8: N-[(2,3-Dimethylphenoxy)thioacetyl]-N'-isopropyl-ethane-1,2-diamine MPt 61°-3°

EXAMPLE 9: N-[(2,3-Dimethylphenoxy)thioacetyl]-N'-benzylethane-1,2-diamine MPt 61°-4°

EXAMPLE 10: N-[(2,3-Dimethylphenoxy)thioacetyl]-N'-octadecyl-ethane-1,2-diamine MPt 66°-7°

EXAMPLE 11: N-[(2,3-Dimethylphenoxy)thioacetyl]-N'-phenyl-ethane-1,2-diamine MPt 65°-6°

EXAMPLE 12: N-[(2,3-Dimethylphenoxy)thioacetyl]-N'-phenyl-N'-methyl-ethane-1,2-diamine MPt 123°-125°

EXAMPLE 13: N-[(2,3-Dimethylphenoxy)thioacetyl]-N',N'-diethyl-ethane-1,2-diamine MPt 49°

EXAMPLE 14: N-[(2,3-Dimethylphenoxy)thioacetyl]-N',N'-dibenzyl-ethane-1,2-diamine MPt 72°-73°

EXAMPLE 15: N-[2-(Pyrrolidino)ethyl]-2-(phenoxy)-thiopropionamide MPt 74°-5°

EXAMPLE 16: N-[2-(Pyrrolidino)ethyl]-2-(2,3-dimethylphenoxy)thio-butyramide (oil)

EXAMPLE 17: N-[2-(Pyrrolidino)ethyl]-2-(2,3-dimethylphenylamino)-thio-acetamide MPt 119°-121°

EXAMPLE 18

Engorged female ticks of the Biarra Strain of *Boophilus microplus* are immersed in groups of 20 ticks per concentration in a range of dilutions of the compound under test. The wash is prepared immediately prior to the test by dilution (with water) of the compound under test. The constituents may be in the form of miscible oil or wettable powder formulation. The desired range of concentrations for the test is obtained by further dilution of the master solution or wash.

The ticks are removed from the wash after 10 minutes, dried, and stuck dorsal side down on double-sided adhesive tape. They remain in this position for 14 days when the proportions of viable eggs laid are determined. From this data a regression line is plotted (concentration against % inhibition of viable egg production) and the IR50 (concentration at which 50% inhibition of viable egg production occurs) is determined.

TABLE I

| Compound of Example No | IR50 (%) |
|---|---|
| 1 | 0.00054 |
| 2 | 0.00016 |
| 3 | 0.002 |
| 4 | 0.0012 |
| 6 | 0.0042 |

EXAMPLE 19

Test compounds were formulation in polyethyleneglycol and 0.622 µl was injected into ticks at a site just ventral to the mouth parts. After 14 days the percentage inhibition of viable egg production (IR) was determined. The results are shown in Table 2 below.

TABLE 2

| Compound of Example No. | % IR at 1 mg/ml |
|---|---|
| 1 | 60 |
| 2 | 90 |
| 3 | 70 |
| 4 | 60 |
| 6 | 60 |

EXAMPLE 20

Wettable powder

| | |
|---|---|
| Active compound | 25.0 parts by weight |
| Kaolin | 69.5 parts by weight |
| Sodium Alkyl Naphthalenesulphonate | 2.6 parts by weight |

-continued

| Sodium Salt of condensed Naphthalene Sulphonic acid | 3.0 parts by weight |
|---|---|
| | 100.0 |

EXAMPLE 21

Aqueous suspension

| Active compound | 50.0 parts by weight |
|---|---|
| Sodium carboxy methyl Cellulose | 0.5 parts by weight |
| Calcium lignosulphonate | 5.0 parts by weight |
| para-Chloro-meta-cresol | 0.2 parts by weight |
| Water | 44.3 parts by weight |
| | 100.0 |

EXAMPLE 22

Paste

| Active compound | 45.0 parts by weight |
|---|---|
| Glycerol | 5.0 parts by weight |
| Xanthan Gum | 2.5 parts by weight |
| Methyl para-Hydroxy-Benzoic Acid | 0.2 parts by weight |
| Fine Silica | 5.0 parts by weight |
| Water | 42.3 parts by weight |
| | 100.0 |

EXAMPLE 23

Pour-on

| Active compound | 2.0 parts by weight |
|---|---|
| Corn oil | 83.0 parts by weight |
| Iso-propanol | 15.0 parts by weight |
| | 100.0 |

EXAMPLE 24

Dust

| Active compound | 1.0 parts by weight |
|---|---|
| Talc | 99.0 parts by weight |
| | 100.0 |

EXAMPLE 25

Grease

| Active compound | 1.5 parts by weight |
|---|---|
| White petroleum jelly | 8.5 parts by weight |
| | 100.0 |

EXAMPLE 26

Aqueous Solution

| Active compound | 10.0 parts by weight |
|---|---|
| Ethylan KEO | 0.5 parts by weight |
| Deionised water | 89.5 parts by weight |
| | 100.0 |

EXAMPLE 27

Water-Miscible Oil

| Active compound | 10.0 parts by weight |
|---|---|
| Ethylan KEO | 20.0 parts by weight |
| Esso 200 | 70.0 parts by weight |
| | 100.0 |

We claim:

1. A compound of formula (I):

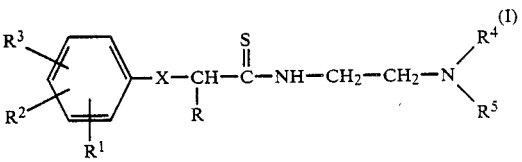

wherein
$R^1$, $R^2$ and $R^3$ are the same or different and are selected from hydrogen, alkyl, alkoxy, halo, cyano and trifluoromethyl, or two of $R^1$, $R^2$, and $R^3$ are linked to form a 3 or 4 carbon atom group;
X is O or NA where A is hydrogen or alkyl;
R is hydrogen or alkyl; and
$R^4$ and $R^5$ are the same or different and are selected from hydrogen; alkyl; substituted alkyl wherein the substituent(s) are selected from halo, cyano, alkoxy, aryloxy, alkylthio, arylthio and substituted and unsubstituted amino; alkenyl, haloalkenyl; aryl; aralkyl or substituted aryl or aralkyl wherein the substituents are selected from halo, alkoxy, cyano and trifluoromethyl; or $NR^4R^5$ is pyrrolidino or piperidino; or an acid addition salt thereof; in the above alkyl and alkoxy have 1 to 20 carbon atoms, aryl is phenyl or naphthyl, aralkyl is alkyl of 1 to 20 carbons substituted by phenyl or naphthyl, and alkenyl has 3 to 20 carbons.

2. A compound according to claim 1 wherein at least one of $R^1$, $R^2$ and $R^3$ is alkyl or halo.

3. A compound according to claim 2 wherein at least one of $R^1$, $R^2$ and $R^3$ is methyl or chloro.

4. A compound according to claim 1 wherein $R^3$ is hydrogen and $R^1$ and $R^2$ are in the 2- and 3-positions.

5. A compound according to claim 4 wherein $R^1$ and $R^2$ are both methyl.

6. A compound according to claim 5 wherein X is O.

7. A compound according to claim 5 wherein X is NH.

8. A compound according to claim 1 wherein $R^4$ is hydrogen or alkyl.

9. A compound according to claim 1 wherein $R^4$ is hydrogen or alkyl.

10. A compound according to claim 1 wherein $R^4$ is hydrogen or alkyl.

11. A compound according to claim 1 wherein $R^5$ is alkyl.

12. N-[(2,3-Dimethylphenoxy)-thioacetyl]-ethane-1,2-diamine or a salt thereof.

13. N-(2-Pyrrolidinoethyl)-(2,3-dimethylphenoxy)-thioacetamide or a salt thereof.

14. N-[(2,3-Dimethoxyphenoxy)-thioacetyl]-N'-methyl-ethane-1,2-diamine or a salt thereof.

15. N-[(2,3-Dimethyphenoxy)-thioacetyl]-N',N'-dimethylethane-1,2-diamine or a salt thereof.

16. N-(2-Piperidinoethyl)-(2,3-dimethylphenoxy)-thioacetamide or a salt thereof.

17. A pesticidal formulation comprising an effective anthropod pest control amount of a compound

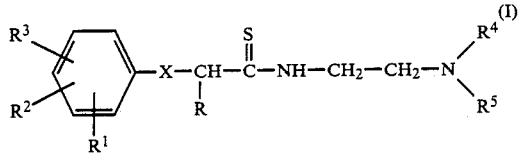

wherein
$R^1$, $R^2$ and $R^3$ are the same or different and are selected from hydrogen, alkyl, alkoxy, halo, cyano and trifluoromethyl, or two of $R^1$, $R^2$ and $R^3$ are linked to form a 3 or 4 carbon atom group;
X is O or NA where A is hydrogen or alkyl;
R is hydrogen or alkyl; and
$R^4$ and $R^5$ are the same or different and are selected from hydrogen; alkyl; substituted alkyl wherein the substituent(s) are selected from halo, cyano, alkoxy, aryloxy, alkylthio, arylthio and substituted and unsubstituted amino; alkenyl, haloalkenyl; aryl; aralkyl or substituted aryl or aralkyl wherein the substituents are selected from halo, alkoxy, cyano and trifluoromethyl; or $NR^4R^5$ or an acid addition salt thereof; in the above alkyl and alkoxy have 1 to 20 carbon atoms, aryl is phenyl or naphthyl, aralkyl is alkyl of 1 to 20 carbons substituted by phenyl or naphthyl, and alkenyl has 3 to 20 carbons and one or more carriers.

18. A formulation according to claim 17 in the form of an aqueous or non-aqueous solution or suspension, miscible oil, wettable powder, dust, granules, powder, paste, grease or gel.

19. A method for the control of anthropod pests comprising the application to the pest or its environment of an effective anthropod pest control amount of a compound of formula (I):

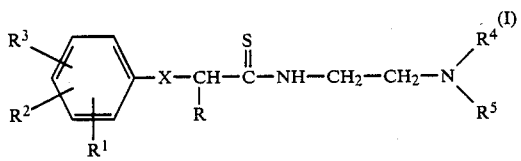

wherein
$R^1$, $R^2$ and $R^3$ are the same or different are selected from hydrogen, alkyl, alkoxy, halo, cyano and trifluoromethyl, or two of $R^1$, $R^2$ and $R^3$ are linked to form a 3 or 4 carbon atom group;
X is O or NA where A is hydrogen or alkyl;
R is hydrogen or alkyl; and
$R^4$ and $R^5$ are the same or different and are selected from hydrogen; alkyl substituted alkyl wherein the substituent(s) are selected from halo, cyano, alkoxy, aryloxy, alkylthio, arylthio and substituted and unsubstituted amino; alkenyl, haloalkenyl; aryl; aralkyl or substituted aryl or aralkyl wherein the substituents are selected from halo, alkoxy, cyano and trifluoromethyl; or $NR^4R^5$; or an acid addition salt thereof; in the above alkyl and alkoxy have 1 to 20 carbon atoms, aryl is phenyl or naphthyl, aralkyl is alkyl of 1 to 20 carbons substituted by phenyl or naphthyl, and alkenyl has 3 to 20 carbons.

20. A method according to claim 19 wherein the pest is an acarine ectoparasite of animals.

21. A method for the control of anthropod pests comprising the application to the pest or its environment of an effective anthropod pest control amount of a formulation as defined in claim 17.

22. A method according to claim 21 wherein the pest is an acarine ectoparasite of animals.

23. A formulation according to claim 17 wherein at least one of $R^1$, $R^2$ and $R^3$ is alkyl or halo.

24. A formulation according to claim 23 wherein at least one of $R^1$, $R^2$ and $R^3$ is methyl or chloro.

25. A formulation according to claim 17 wherein $R^3$ is hydrogen and $R^1$ and $R^2$ are in the 2- and 3-positions.

26. A formulation according to claim 25 wherein $R^1$ and $R^2$ are both methyl.

27. A formulation according to claim 25 wherein X is O.

28. A formulation according to claim 25 wherein X is NH.

29. A formulation according to claim 17 wherein $R^4$ is hydrogen or alkyl.

30. A formulation according to claim 25 wherein $R^4$ is hydrogen or alkyl.

31. A formulation according to claim 25 wherein $R^4$ is hydrogen or alkyl.

32. A formulation according to claim 17 wherein $R^5$ is alkyl.

33. A formulation according to claim 17 which the compound or salt is N-[(2,3-Dimethylphenoxy)-thioacetyl]-ethane-1,2-diamine or a salt thereof.

34. A formulation according to claim 17 in which the compound or salt is N-(2-Pyrrolidinoethyl)-(2,3-dimethylphenoxy)thio-acetamide or a salt thereof.

35. A formulation according to claim 17 in which the compound or salt is N-[(2,3-Dimethoxyphenoxy)-thioacetyl]-N'-methyl-ethane-1,2-diamine or a salt thereof.

36. A formulation according to claim 17 in which the compound or salt is N-[(2,3-Dimethyphenoxy)-thioacetyl]-N',N'-dimethyl-ethane-1,2-diamine or a salt thereof.

37. A formulation according to claim 17 in which the compound or salt is N-(2-Piperidinoethyl)-(2,3-dimethylphenoxy)thioacetamide or a salt thereof.

38. A formulation according to claim 17 in which $R^4$ and $R^5$ are hydrogen.

39. A method according to claim 19 wherein at least one of $R^1$, $R^2$ and $R^3$ is alkyl or halo.

40. A method according to claim 39 wherein at least one of $R^1$, $R^2$ and $R^3$ is methyl or chloro.

41. A method according to claim 19 wherein $R^3$ is hydrogen and $R^1$ and $R^2$ are in the 2- and 3-positions.

42. A method according to claim 41 wherein $R^1$ and $R^2$ are both methyl.

43. A method according to claim 42 wherein X is O.

44. A method according to claim 42 wherein X is NH.

45. A method according to claim 19 wherein $R^4$ is hydrogen or alkyl.

46. A method according to claim 43 wherein $R^4$ is hydrogen or alkyl.

47. A method according to claim 44 wherein $R^4$ is hydrogen or alkyl.

48. A method according to claim 19 wherein $R^5$ is alkyl.

49. A method according to claim 19 in which the compound or salt is N-[(2,3-Dimethylphenoxy)-thioacetyl]-ethane-1,2-diamine or a salt thereof.

50. A method according to claim 19 in which the compound or salt is N-(2-Pyrrolidinoethyl)-(2,3-dimethylphenoxy)-thioacetamide or a salt thereof.

51. A method according to claim 19 in which the compound or salt is N-[(2,3-Dimethyphenoxy)-thioacetyl]-N'-methyl-ethane-1,2-diamine or a salt thereof.

52. A method according to claim 19 in which the compound or salt is N-[(2,3-Dimethyphenoxy)-thioacetyl]-N',N'-dimethylethane-1,2-diamine or a salt thereof.

53. A method according to claim 19 in which the compound or salt is N-(2-Piperidinoethyl)-(2,3-dimethylphenoxy)thioacetamide or a salt thereof.

54. A method according to claim 19 in which $R^4$ and $R^5$ are hydrogen.

* * * * *